(12) United States Patent
Hall et al.

(10) Patent No.: US 10,409,960 B2
(45) Date of Patent: Sep. 10, 2019

(54) FULL CYCLE REMOTE PHARMACY

(71) Applicants: David R. Hall, Provo, UT (US); Dan Allen, Springville, UT (US); Ben Swenson, Lehi, UT (US); Conrad Rosenbrock, Provo, UT (US)

(72) Inventors: David R. Hall, Provo, UT (US); Dan Allen, Springville, UT (US); Ben Swenson, Lehi, UT (US); Conrad Rosenbrock, Provo, UT (US)

( * ) Notice: Subject to any disclaimer, the term of this patent is extended or adjusted under 35 U.S.C. 154(b) by 43 days.

(21) Appl. No.: 15/377,048

(22) Filed: Dec. 13, 2016

(65) Prior Publication Data

US 2018/0165421 A1    Jun. 14, 2018

(51) Int. Cl.
*G06F 19/00* (2018.01)
*G16H 40/20* (2018.01)
*G07F 17/00* (2006.01)

(52) U.S. Cl.
CPC ...... *G06F 19/3462* (2013.01); *G06F 19/3418* (2013.01); *G07F 17/0092* (2013.01); *G16H 40/20* (2018.01)

(58) Field of Classification Search
CPC .................................................. G07F 17/0092
See application file for complete search history.

(56) References Cited

U.S. PATENT DOCUMENTS

| | | | | |
|---|---|---|---|---|
| 5,036,462 A * | 7/1991 | Kaufman | ............... | A61J 7/0084 600/300 |
| 8,195,328 B2 * | 6/2012 | Mallett | ................... | A61L 11/00 221/102 |
| 8,473,097 B2 * | 6/2013 | Shoenfeld | ................. | A61L 2/10 221/282 |
| 2003/0050731 A1 * | 3/2003 | Rosenblum | ......... | G06F 19/3462 700/232 |
| 2007/0186923 A1 * | 8/2007 | Poutiatine | ............. | A61J 7/0038 128/200.14 |
| 2008/0272138 A1 * | 11/2008 | Ross | ................... | G06F 19/3462 221/1 |
| 2010/0112180 A1 * | 5/2010 | Laniado | ................ | A47J 31/401 426/590 |
| 2011/0054668 A1 * | 3/2011 | Holmes | ............ | G06Q 20/40145 700/216 |
| 2012/0004770 A1 * | 1/2012 | Ooyen | ................ | G06F 19/3462 700/235 |

(Continued)

*Primary Examiner* — Timothy R Waggoner

(57) ABSTRACT

We disclose a telemedicine device for tracking, dispensing, and retrieving medical supplies as well as methods of its use. The device includes a medical supply dispensing and retrieving station which includes a medical supply dispenser and medical supply receptacle. Both the medical supply dispenser and medical supply receptacle may include multiple compartments which house medical supplies. The device may include a communication port for receiving prescription information. The device includes a personal identification indicator which verifies the identity of the user and links the identity to the user's prescription information. The device may include medical devices. The medical devices may conduct measurements to confirm efficacy of a medical supply or screen for side effects. The device may confirm proper usage of a medical supply by weighing an unused portion of the medical supply and comparing it to the weight expected for the amount that should be remaining.

14 Claims, 9 Drawing Sheets

(56) References Cited

U.S. PATENT DOCUMENTS

2014/0278510 A1\* 9/2014 McLean ................ A61J 7/0076
  705/2
2017/0326033 A1\* 11/2017 Kraft ..................... A61J 7/0084

\* cited by examiner

FULL CYCLE REMOTE PHARMACY

BACKGROUND

Field of the Invention

This disclosure relates to equipment and methods for dispensing medical supplies using an automated system.

Background of the Invention

While a healthcare provider may prescribe the proper medication to a patient, the patient may not take the medication as instructed. The healthcare system is not equipped to closely monitor patients to confirm the proper consumption of medications. Alternatively, medications may cause dangerous side-effects or be ineffective for a particular patient. Some patients may neglect to return to the healthcare provider in these situations due to inconvenience or being unaware of the need. An automated method of tracking medication consumption is needed. A convenient way to follow-up the efficacy and safety of a medication is also needed. In addition, a convenient method to collect unused medications for proper disposal is also needed.

BRIEF SUMMARY OF THE INVENTION

We disclose a medical supply dispensing and retrieving station which functions as a full cycle remote pharmacy. The medical supply dispensing and retrieving station includes a medical supply dispenser and a medical supply receptacle, each of which may include a plurality of compartments. The compartments within the medical supply dispenser may be stocked with medical supplies, including medications, wound care supplies, and medical devices. The medical supply dispensing and retrieving station may require a user to present a personal identification indicator to a user validation device before receiving medical supplies. This step may confirm that the user is authorized to receive the medical supplies.

The medical supply dispensing and receiving station may include at least one communication port through which it may communicate with a remote entity. The medical supply dispensing and receiving station may receive prescription information from remote healthcare providers through the communication port. Users may receive the medical supplies authorized by the prescription through the medical supply dispenser.

Users may also return to the medical supply dispensing and receiving station to submit their partially used medical supply for weighing to confirm proper use over time. The medical supply dispensing and receiving station may include biometric measurement devices. A user may conduct biometric measurements to confirm efficacy of the medical supply and to screen for side effects caused by the medical supply.

Users may return unused and unwanted medical supplies to the medical supply dispensing and receiving station for proper destruction or refurbishment. Users who are not clients of the medical supply dispensing and receiving station may also return medical supplies to the medical supply dispenser to avoid their improper use.

The disclosed medical supply dispensing and receiving station may provide convenient dispensing and return of medical supplies and, in some instances, avoid adverse events or trips to a staffed clinic.

DETAILED DESCRIPTION OF THE INVENTION

Definitions

Figure 1A:
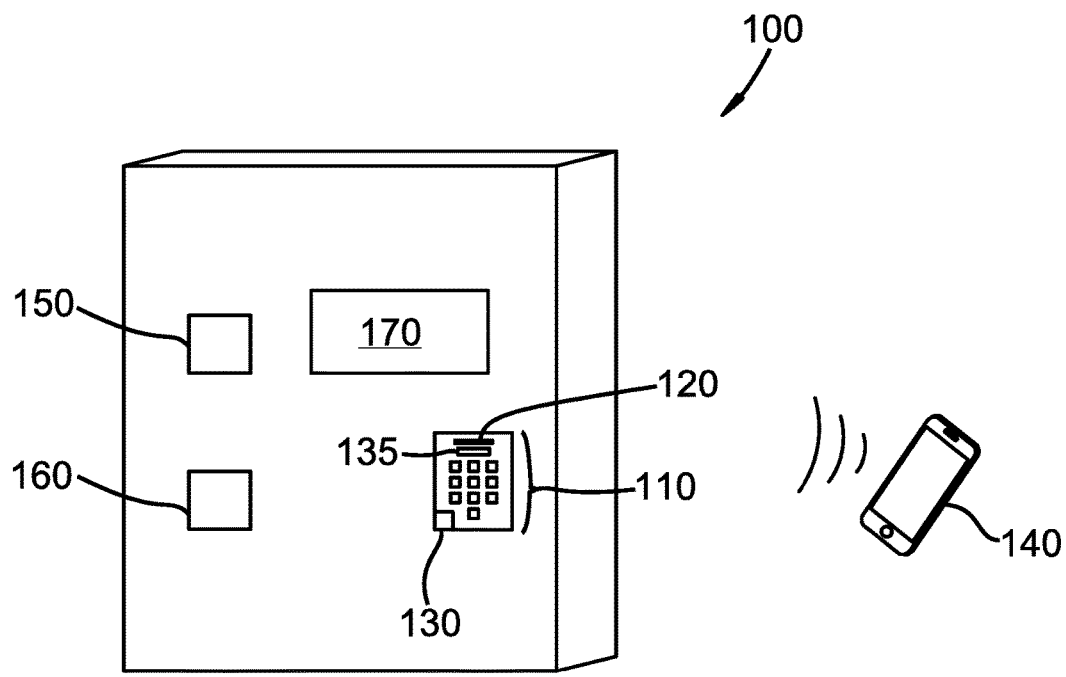
FIG. 1A illustrates a medical supply dispensing and retrieving station kiosk according to an embodiment of the disclosed medical supply dispensing and retrieving station.

User, as used herein, means any mammal, human or animal, for which the medical supply dispensing and retrieving station disclosed herein is used to provide medical supplies.

Healthcare provider, as used herein, means any individual who performs a task, mental or physical, in relation to health-related services provided to a user. In addition to clinicians who practice medicine directly on a user, the term healthcare provider includes any person that enters data into a computer, when the data entry is used in analysis of a user's health status or to improve a user's health.

While this invention is susceptible of embodiment in many different forms, there are shown in the drawings, which will herein be described in detail, several specific embodiments with the understanding that the present disclosure is to be considered as an exemplification of the principals of the invention and is not intended to limit the invention to the illustrated embodiments.

We disclose a medical supply dispensing and retrieving station (hereinafter, the "station") which enables a user to receive and return medical supplies, including, but not limited to, prescription medication. The station receives and dispenses prescriptions for medical supplies through telemedicine methods. The station may resemble a kiosk, cabinet, vending machine, or robotic pharmacy which has at least one communication port to allow the user and the station to communicate with remote entities. The remote entities may include a telemedicine center, a remote healthcare facility, a remote healthcare provider, and a security facility.

The station may include a medical supply dispenser which may resemble a cabinet with multiple compartments. The compartments of the medical supply dispenser house medical supplies including, but not limited to, prescription medication, over-the-counter medication, a medical treatment device, a pharmaceutical delivery device, a medical diagnostic device, a medical alert tag, urinary catheters, wound care supplies, bandages, and other supplies useful to treat or diagnose an illness or injury. The compartments of the medical supply dispenser may be connected to a dispenser opening located on the outside of the station. The dispenser opening may resemble the opening in a vending machine used to retrieve product. The compartments of the medical supply dispenser may be connected to the dispenser opening through a means which may be a chute or tunnel through which medical supplies travel from the compartment to the dispenser opening. The user may retrieve the medical supply from the dispenser opening.

The station may also include a medical supply receptacle which may resemble a cabinet with multiple compartments. The compartments of the medical supply receptacle may store medical supplies that a user has returned. The compartments of the medical supply receptacle may be connected to a receptacle opening located on the outside of the station. The compartments in the medical supply receptacle may be connected to the receptacle opening through a means which may be a chute or tunnel through which returned medical supplies may travel from the receptacle opening to the compartments of the medical supply receptacle. In some embodiments, the cabinet housing the compartments of the medical supply dispenser may also house the compartments of the medical supply receptacle. In some embodiments, the medical supply receptacle includes a means for sterilizing returned medical supplies. The means for sterilization may include chemical sterilization, radioactive exposure, exposure to ultraviolet light, or autoclaving.

Both the compartments in the medical supply dispenser and the medical supply receptacle may provide secure containment of the medical supplies within. Accordingly, those wishing to steal the medical supplies from the station may not easily acquire them. Security measures may include those known in the art for securing valuables and controlled substances including, but not limited to, alarms, steel barriers, and locks.

The packaging surrounding the medical supplies in the station may be tagged with a medical supply code which is unique each medical supply. The station may include a scanner which scans the medical supply code to identify the medical supply when it enters the station upon return by a user. The scanner may also scan the medical supply code to confirm its identity as it leaves the station to be received by a user.

The station may include a user validation device. Each user may be given a personal identification indicator. The user validation device may validate the identity of each valid user. Each time a user approaches the station to fill a prescription, the user presents the unique personal identification indicator to the user validation device. The user may also present the unique personal identification indicator to the user validation device when returning a medical supply or presenting a medical supply to confirm the amount that has been used or consumed by a given date. The personal identification indicator may include one or more of a Bluetooth beacon, personal identification code, a token, a magnetic stripe card, radio frequency identification of a user's mobile device, and biometric verification. In some embodiments, a user may be authorized to receive a medical supply that is authorized for another person, for example, a child, dependent, or ward.

The station may include a scale which may measure a weight of a medical supply before the medical supply is dispensed to a user, when a user returns a medical supply, or both. The controller may record the difference between the two weights to estimate the amount of medical supply that has been used or consumed. This data may be sent to a remote entity through the communication port in the station. In some circumstances, the remote entity may respond to the information about the difference in the two weights with a communication that dictates whether the station will return the unused medical supply to the user or if it will refill a prescription.

The station may include one or more biometric measuring device. The one or more biometric measuring device may be used to confirm whether a user is experiencing a side effect from the medical supply or to assess the efficacy of the medical supply for that user. The one or more biometric measuring device may include one or more of the following: a heart rate monitor, a blood pressure monitor, a weight sensor, a bioimpedance sensor, a glucometer, a blood analyzer, an electrocardiogram unit, a respirometer, a respiratory rate monitor, a body temperature sensor, an otoscope, a stethoscope, a pulse oximeter, an ophthalmoscope, an ultrasound device, a test strip, a test strip reader, a tissue collector, and imaging device for creating a visual reading.

In practice, a healthcare provider may send an electronic signal to the station which includes a user's prescription for a medical supply. The information may be stored in the controller. The information may include an authorization code which identifies the medical supply authorized by the prescription. The user for which the prescription was sent may be given a personal identification indicator. The information in the controller may link the user's personal identification indicator with the prescription information to ascertain that the user is authorized to receive the medical supply. When a user wishes to fill the prescription, the user may approach the station and present the user's personal identification indicator to the user validation device. The user validation device verifies the user's identity and links that information to the user's prescription information. If the user desires, the user may communicate with a remote healthcare provider through an audiovisual device within the station to ask questions.

The code scanner may scan the medical supply code on the medical supply the user is authorized to receive to confirm that it is the correct medical supply. The medical supply dispenser may then transfer the medical supply from the compartment in which is stored to the dispenser opening. The user may retrieve the medical supply from the dispenser opening.

In some instances, the user may return to the station with a partially used medical supply or the packaging of a completely used medical supply. An example of a situation in which a user may return with a partially used medical supply is when a healthcare provider asks the user to periodically use the station to confirm the amount of the medical supply that has been used or consumed. The healthcare provider may ask the user to perform this task to assure that the user is following the prescription instructions. In this example, the user may again approach the station and present the user's personal identification indicator to the user validation device. The user validation device verifies the user's identity and links that information to the user's prescription information. The user may deposit the partially used medical supply or the packaging from a completely used medical supply into the receptacle opening of the medical supply receptacle. The code scanner may scan the medical supply code on the medical supply packaging to identify the medical supply. The scale may weigh the partially used medical supply or the packaging from a completely used medical supply and send the measurement to the controller. The controller may compare the weight measurement to the weight of the medical supply before it was dispensed to the user. The controller may use the difference in the two weight measurements to estimate how much of the medical supply was used or consumed. The station may then return the unused portion of the medical supply to the user for continued use or consumption.

In some situations, for example, when a user has consumed too much of a medication, the controller may be programmed not to return the unused portion of the medical supply. In this example, the medical supply may be stored in a compartment within the medical supply receptacle for either destruction or refurbishment to be reused.

Another example of an instance when a user may return with a partially used medical supply is when the medical supply may cause a dangerous side effect or may not be effective for the user. In this situation, the user may be instructed through the audiovisual device to use a biometric measurement device which may be associated with the station to collect a biometric measurement. The user may conduct the biometric measurement and the result may be sent to the controller within or associated with the station. If the biometric measurement is within a defined range, the station may return the medical supply to the user. If the biomedical measurement is outside of a defined range, the station may not return the medical supply to the user and transfer it to a compartment within the medical supply receptacle. The user may receive a message through a mobile device or through an audiovisual device on the station instructing the user to contact a healthcare provider.

Another response to a biometric reading that is outside a defined range is that the station may dispense an alternative medical product or change the user's dose. This may be accomplished by transmitting the biometric measurement to a remote healthcare provider who then sends a signal to the station authorizing the change. The alternative medical product may be dispensed in a manner similar to the method followed when the original prescription was filled. If the user is to use the same product but follow a different dosing schedule, the station may provide a printout of the new dosing schedule. The user may also communicate with a remote healthcare provider through an audiovisual device associated with the station to clarify the new instructions.

A similar process may be followed to refill a prescription for a medical supply. In an example, the user may approach the station present the user's personal identification indicator to the user validation device. The user validation device may verify the user's identity and link that information to the user's prescription information. If the prescription information indicates that the user may refill the prescription, the station proceeds to supply the medical supply through the medical supply dispenser as it did when the original prescription was filled. In some embodiments of this method, the station may also ask the user to collect a biometric measurement before dispensing a refill. The station may deny the refill if the biometric measurement is outside a defined range. In this instance, the station may alternatively follow the steps for providing an alternative medical supply or different dosing schedule as described above.

A user may also dispose of unused and unwanted medical supplies through the station. For example, a user may have been prescribed a pain medication that could be dangerous or addictive. The user no longer need the medication and may wish to prevent a child or addicted person from accessing the medication. The user may deposit the unused medical supply in the receptacle opening of the medical supply receptacle. The code scanner may scan the medical supply code on the medical supply packaging to identify the medical supply. The medical supply receptacle may transfer the remaining medical supply to a compartment within the medical supply receptacle for subsequent destruction. This method may include the steps of presenting the user's personal identification indicator to the user validation device so that the source of the unused medical supply is recorded. This method may be useful to confirm that a user is no longer in possession of the medical supply. The station may also be configured to enable users who are not authorized clients to deposit unused medical supplies, including, not limited to, hypodermic needles and dangerous medications, for proper destruction without presenting a personal identification indicator.

In some embodiments, users may be given incentives for returning to the station to confirm proper use of the medical supplies or for returning unused medical supplies for reuse or destruction. In some embodiments, users may be given penalties for failure to return to the station to confirm proper use of medical supplies. The incentives may include discounts on medical supplies, cash payments, discounts on other products, or other in-kind rewards. The penalties may include denial of incentives or denial of access to the station.

In some embodiments, the station includes a method of confirming that the medical supply has been kept within a defined temperature range. This is useful because some medical products, including medications, lose their effectiveness when exposed to extreme temperatures. In one example, the packaging surrounding the medical supply includes a temperature verifier. This may be a device that detects and records the temperature of the air around it and emits a signal that a scanner may detect to transmit this information. Alternatively, the temperature verifier may produce a visual indicator when it has been exposed to temperatures outside a defined temperature range. The station may include a scanner which reads a signal from the temperature verifier. The scanner may detect an electronic or radiofrequency signal or scan a color of the temperature verifier. The controller may flag the medical supply if the signal indicates that the medical supply has been exposed to temperatures outside the defined range. This may indicate that the medical supply is to be destroyed or refurbished before use.

Additionally, the temperature verifier may indicate to the user that the medical device has been exposed to temperatures outside the defined range so that the user may discontinue use and return the medical supply to the station. In this example, the temperature verifier may provide a visual signal that does not require a scanner to read. For example, the temperature verifier may include a sticker on the packaging surrounding the medical supply. Prior to being exposed to temperatures outside the defined range, the sticker may appear as one color or pattern. For example, the sticker may appear red, green, yellow purple, orange, blue gold silver, or combinations thereof. In other embodiments, the sticker may initially include a pattern including, but not limited to, hatches, a drawing, words, dots, or stripes. After exposure to temperatures outside of the defined range, the sticker may appear as a different color or pattern which may be one of those listed herein or other colors or patterns.

Referring now to the drawings, FIG. 1A shows medical supply dispensing and retrieving station 100. This embodiment of the disclosed medical supply dispensing and retrieving station is in the form of a kiosk. Medical supply dispensing and retrieving station 100 includes a medical supply dispenser which includes dispenser opening 150. Users may retrieve a medical supply from the medical supply dispenser by reaching into dispenser opening 150 to grasp the medical supply. Medical supply dispensing and retrieving station 100 also includes a medical supply receptacle which includes receptacle opening 160. A user may deposit medical supplies into receptacle opening 160 to confirm proper consumption of the medication or to return unwanted medical supplies. Medical supply dispensing and retrieving station 100 also includes a user validation device which includes personal identification input plate 110. Personal identification input plate 110 includes multiple methods of providing a personal identification indicator. These include slot 120 for inputting a keycard, pad 135 for tapping a keycard with a radiofrequency identification (RFID) tag, fingerprint scanner 130, and a numerical keypad for typing in a personal identification number (PIN). Mobile device 140 may also emit a radiofrequency identification signal which the user validation device detects. A user may receive or enter information through user communication device 170. In some embodiments, user communication device 170 may be an interactive touch screen. In other embodiments, use communication device may be an audiovisual device which connects directly to a live healthcare provider with whom the user may converse.

Figure 1B:
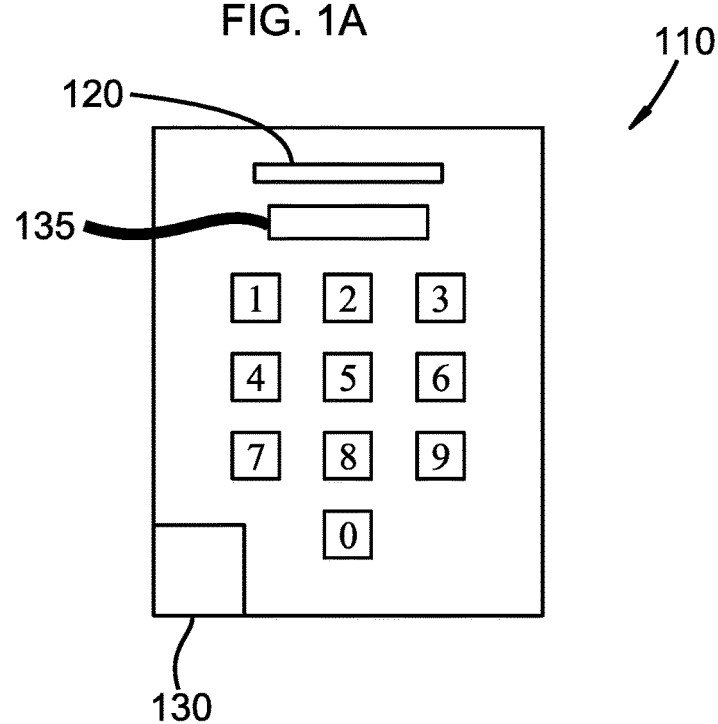
FIG. 1B illustrates an embodiment of a user validation device according to the disclosed medical supply dispensing and retrieving station.

FIG. 1B is a close-up of personal identification input plate 110 of the user validation device presented in FIG. 1A which illustrates the multiple methods of providing a personal identification indicator in greater detail.

Figure 2:
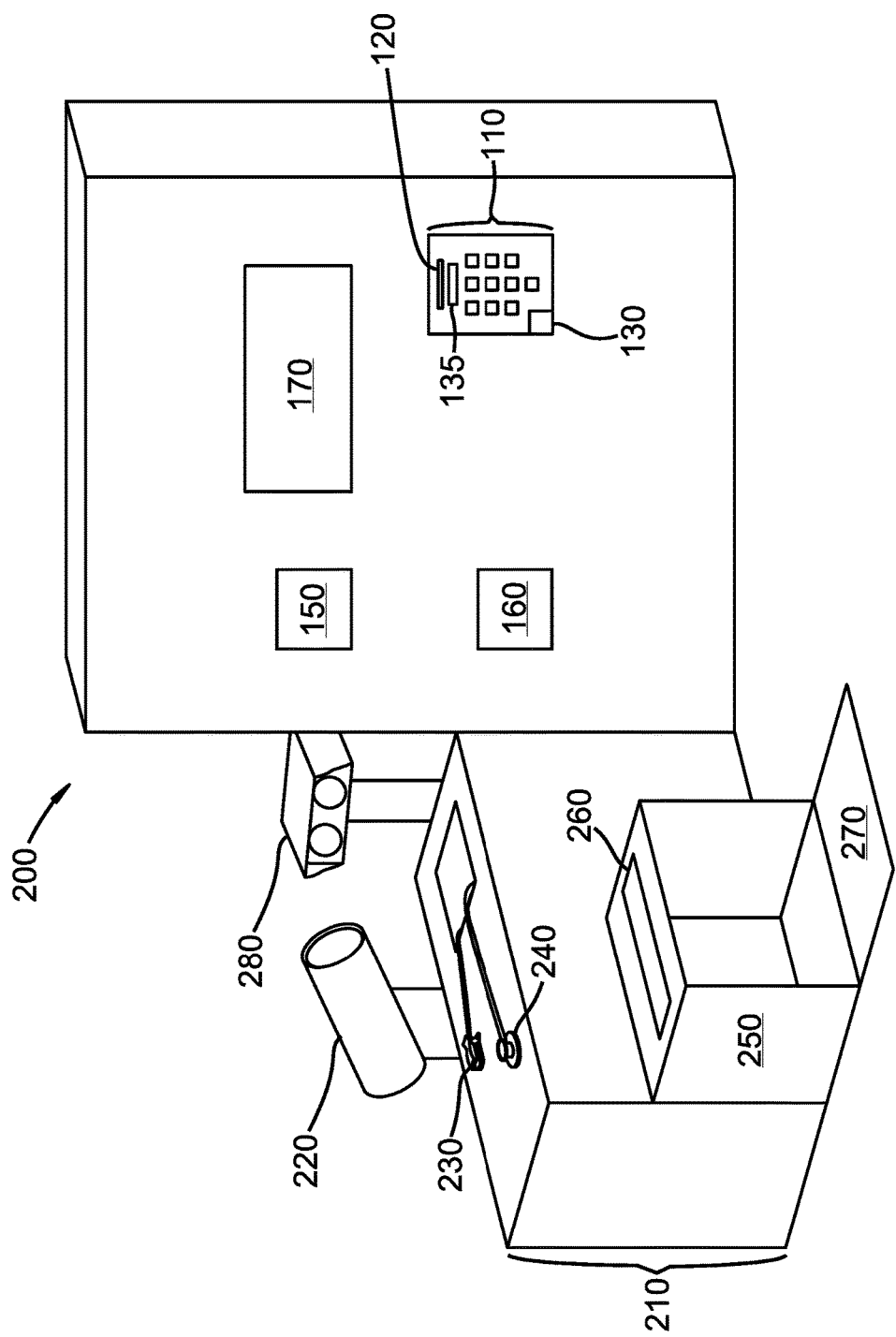
FIG. 2 illustrates a medical supply dispensing and retrieving station including multiple biometric measurement devices according to an embodiment of the disclosed medical supply dispensing and retrieving station.

FIG. 2 illustrates medical supply dispensing and retrieving station 200 which comprises the embodiment of FIG. 1A but which further includes biometric station 210. Biometric station 210 includes multiple biometric measurement devices. The multiple biometric medical devices of this embodiment include blood pressure monitor 220, pulse oximeter 230, stethoscope 240, and ophthalmic diagnostic device 280. Station 210 includes seat 250 where the user may sit while using the medical biometric measurement devices. Seat 250 includes pressure sensor 260 which may collect a body weight measurement along with pressure sensor 270 while the user is seated. Alternatively, the user may stand on pressure sensor 270 to collect a body weight measurement.

Figure 3:
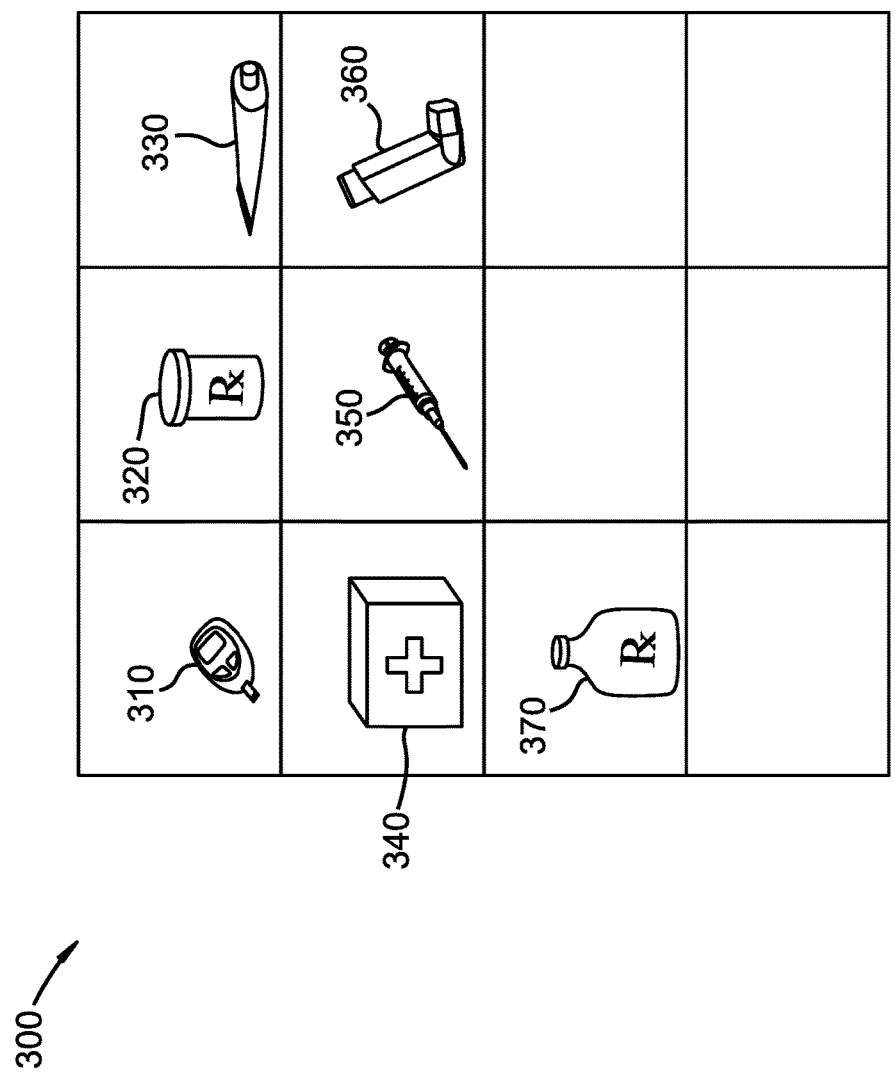
FIG. 3 illustrates an embodiment of a medical supply dispenser according to an embodiment of the disclosed medical supply dispensing and retrieving station.

FIG. 3 is a schematic view of compartment bank 300 that may be within an embodiment of a medical supply dispenser according to the disclosure. Individual compartments within compartment bank 300 include the following: glucometer 300, pill bottle 320, therapeutic cream 330, first aid kit 340, injectable medication 350, inhaler 360, and elixir 370. These are but examples of medical supplies that may be stored in compartment bank 300 and embodiments thereof.

Figure 4:
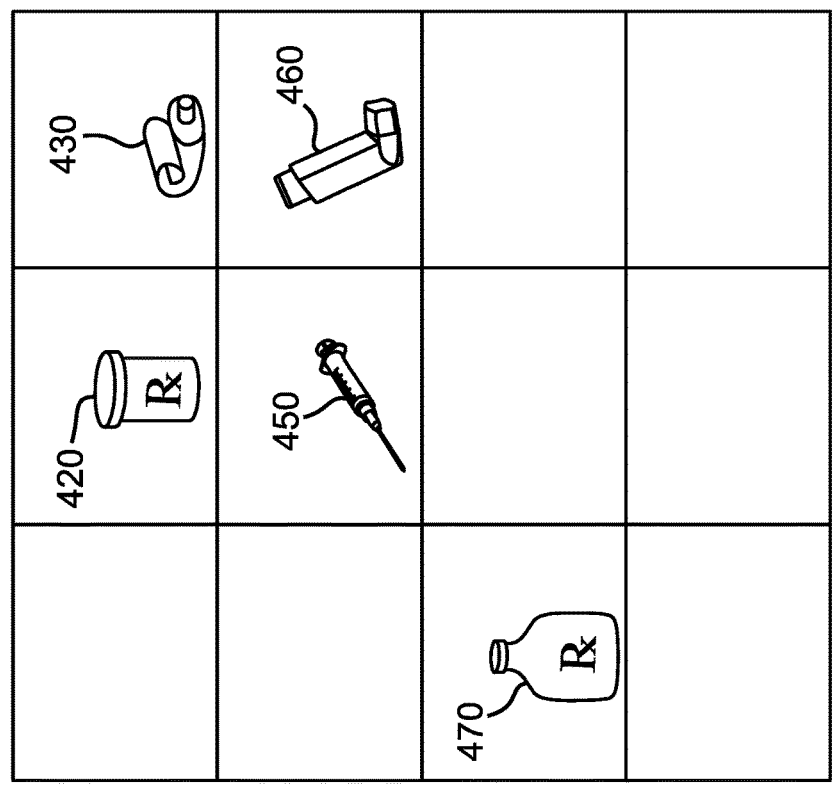
FIG. 4 illustrates an embodiment of a medical supply receptacle according to an embodiment of the disclosed medical supply dispensing and retrieving station.

FIG. 4 is a schematic view of compartment bank 400 that may be within an embodiment of a medical supply receptacle according to the disclosure. Individual compartments within compartment bank 400 include the following used or partially used medical supplies: pill bottle 420, therapeutic cream 430, injectable medication 450, inhaler 460, and elixir 340.

Figure 5:
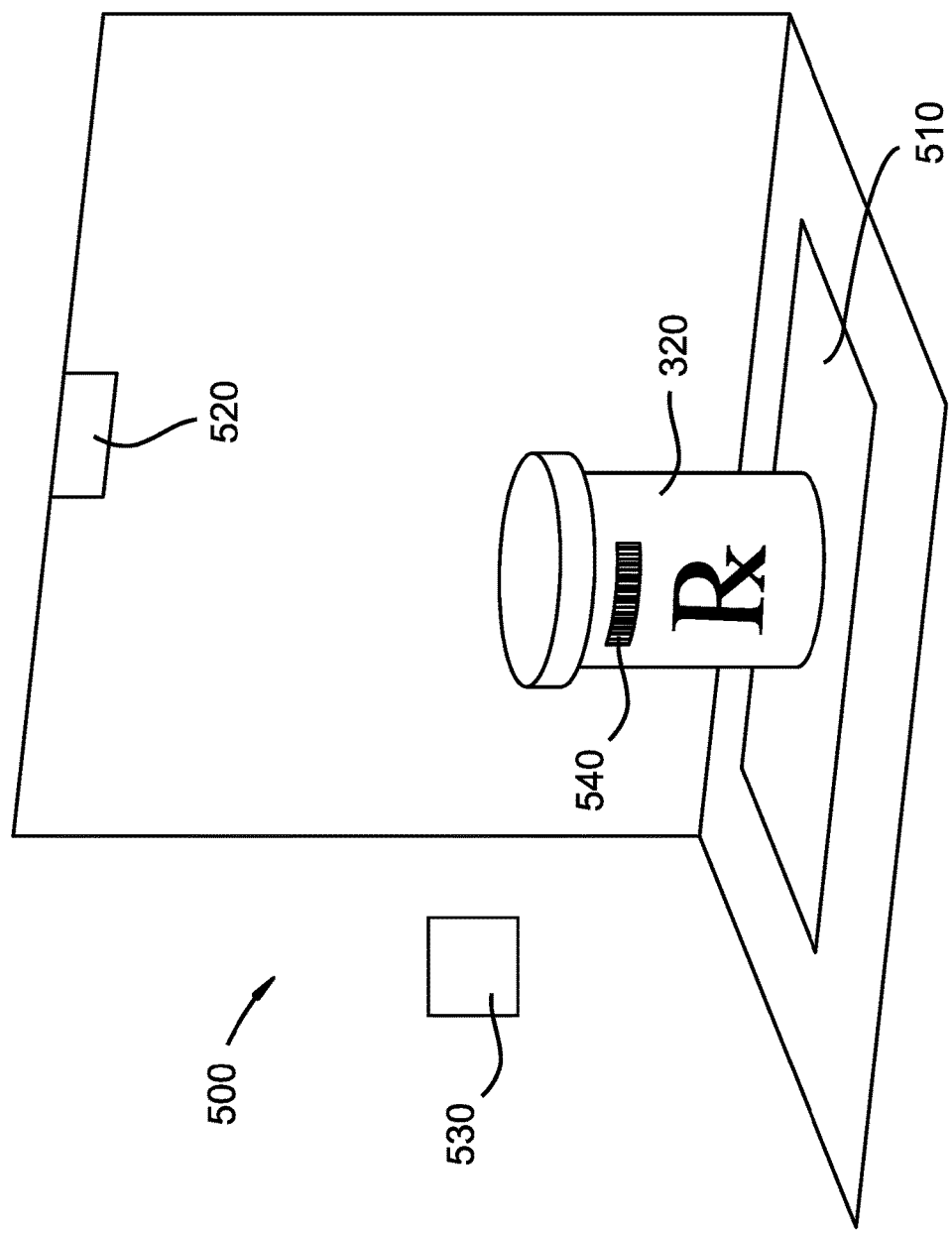
FIG. 5 illustrates an embodiment of a compartment within a medical supply dispenser with a proximity detector according to an embodiment of the disclosed medical supply dispensing and retrieving station.

FIG. 5 is a schematic drawing of compartment 500 which includes multiple methods of identifying pill bottle 320 which has been deposited into a medical supply receptacle according to an embodiment of the disclosure. These include scanner 520 which scans bar code 540 on pill bottle 320 and scanner 530 which detects an RFID tag that is within pill bottle 320. These are but examples of mechanisms to confirm the identity and user of pill bottle 320. Pressure sensor 510 detects the weight of pill bottle 320 and sends the measurement to a controller. The controller compares the current weight of pill bottle 320 with the weight of pill bottle 320 when the user received it. The amount of medication that is missing since the user received pill bottle 320 may then be calculated and compared to the amount that should be missing if the user consumed the mediation as instructed.

Figure 6B:
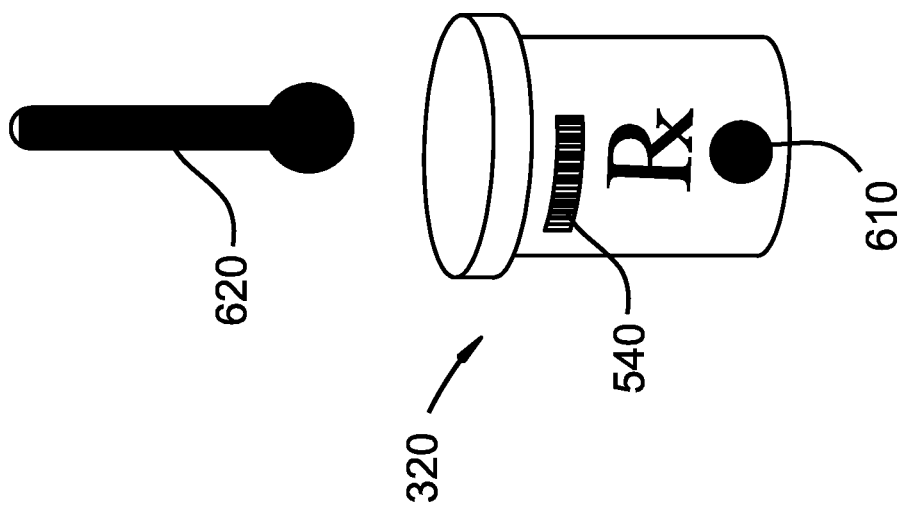
FIG. 6B illustrates the medical supply with temperature verifier of FIG. 6A after the medical supply has been exposed to temperatures outside of a defubed range.
Figure 6A:
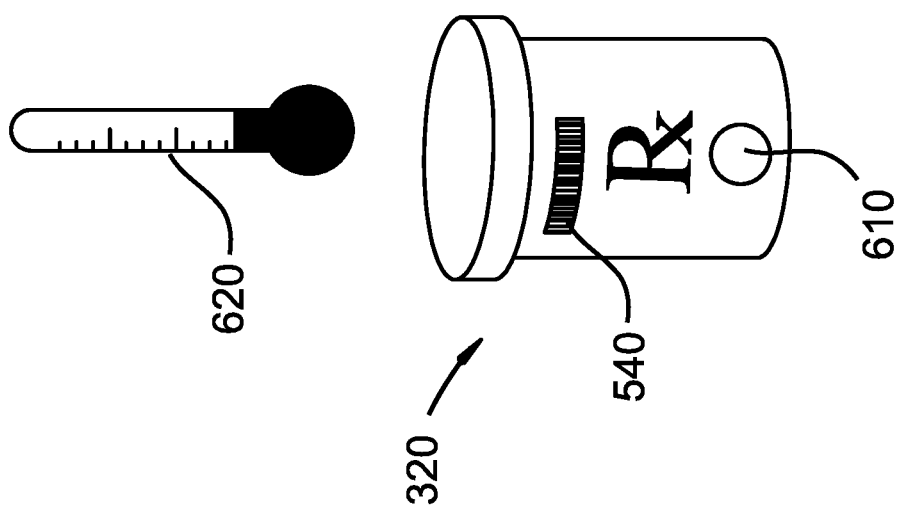
FIG. 6A illustrates an embodiment of a medical supply with a temperature verifier that has been kept within a defined range.

FIG. 6A illustrates pill bottle 320 which includes temperature verifier 610. Thermometer 620 indicates that pill bottle 320 has been stored at a relatively low temperature which is within the recommended temperature range for storage of the medication within pill bottle 320. Accordingly, temperature verifier 610 is shown as a first color which is white in FIG. 6A. In other embodiments, the first color of temperature verifier 610 may be any color including, but not limited to, red, green, yellow, purple, orange, blue, gold, silver, or combinations thereof. In other embodiments, the first color may be a first pattern including, but not limited to, hatches, a drawing, words, dots, or stripes.

FIG. 6B illustrates pill bottle 320 after it has been stored at a higher temperature, as shown by thermometer 620, which is outside a recommended temperature range for storing the medication inside pill bottle 320. Temperature verifier 610 has turned a second color in response to the elevated heat. Accordingly, temperature verifier 610 is shown as a second color which is black in FIG. 6B. In other embodiments, the second color of temperature verifier 610 may be any color including, but not limited to, red, green, yellow, purple, orange, blue, gold, silver, or combinations thereof. In other embodiments, the second color may be a first pattern including, but not limited to, hatches, a drawing, words, dots, or stripes.

Figure 7:
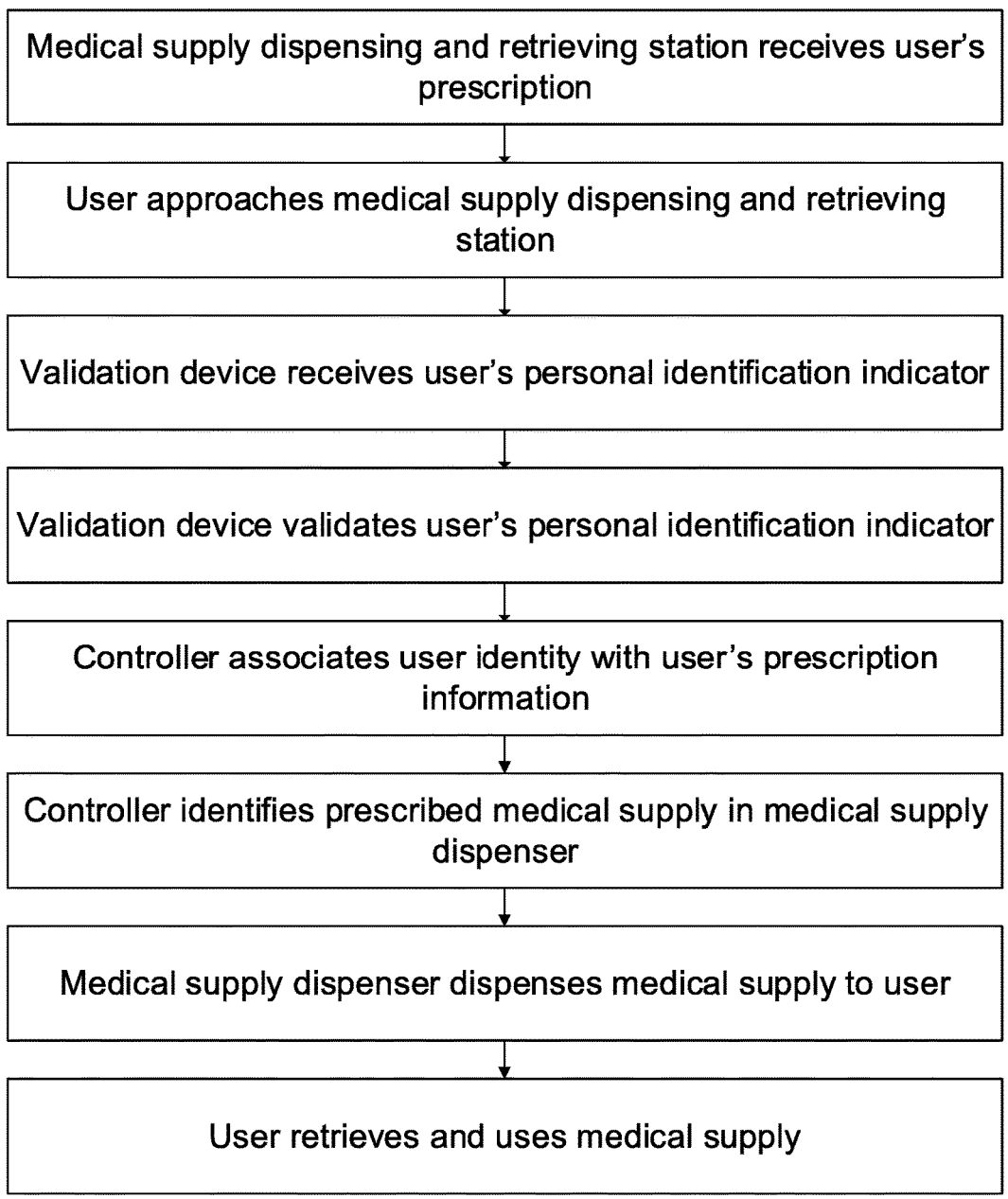
FIG. 7 is a flow chart illustrating a method of using an embodiment of the disclosed medical supply dispensing and retrieving station to retrieve a prescription medication.

FIG. 7 is a flow chart illustrating an embodiment of a method that a user may follow to retrieve a prescription medication from an embodiment of the disclosed medical supply dispensing and retrieving station. In the method of FIG. 7, a controller within the medical supply dispensing and retrieving station receives an electronic signal that communicates a user's prescription information. The electronic signal may have originated from the user's healthcare provider. The user then approaches the medical supply dispensing and retrieving station and enters a personal identification indicator into the validation device on the medical supply dispensing and retrieving station. The validation device confirms the user's identity and links the information to the user's prescription information stored in the controller. The controller then identifies the user's prescribed medical supply within a compartment in the medical supply dispenser. In some embodiments, this step includes scanning the medical supply code on the medical supply to confirm its identity. The medical supply dispenser dispenses the prescribed medial supply to the user. The user then retrieves the medical supply.

Figure 8:
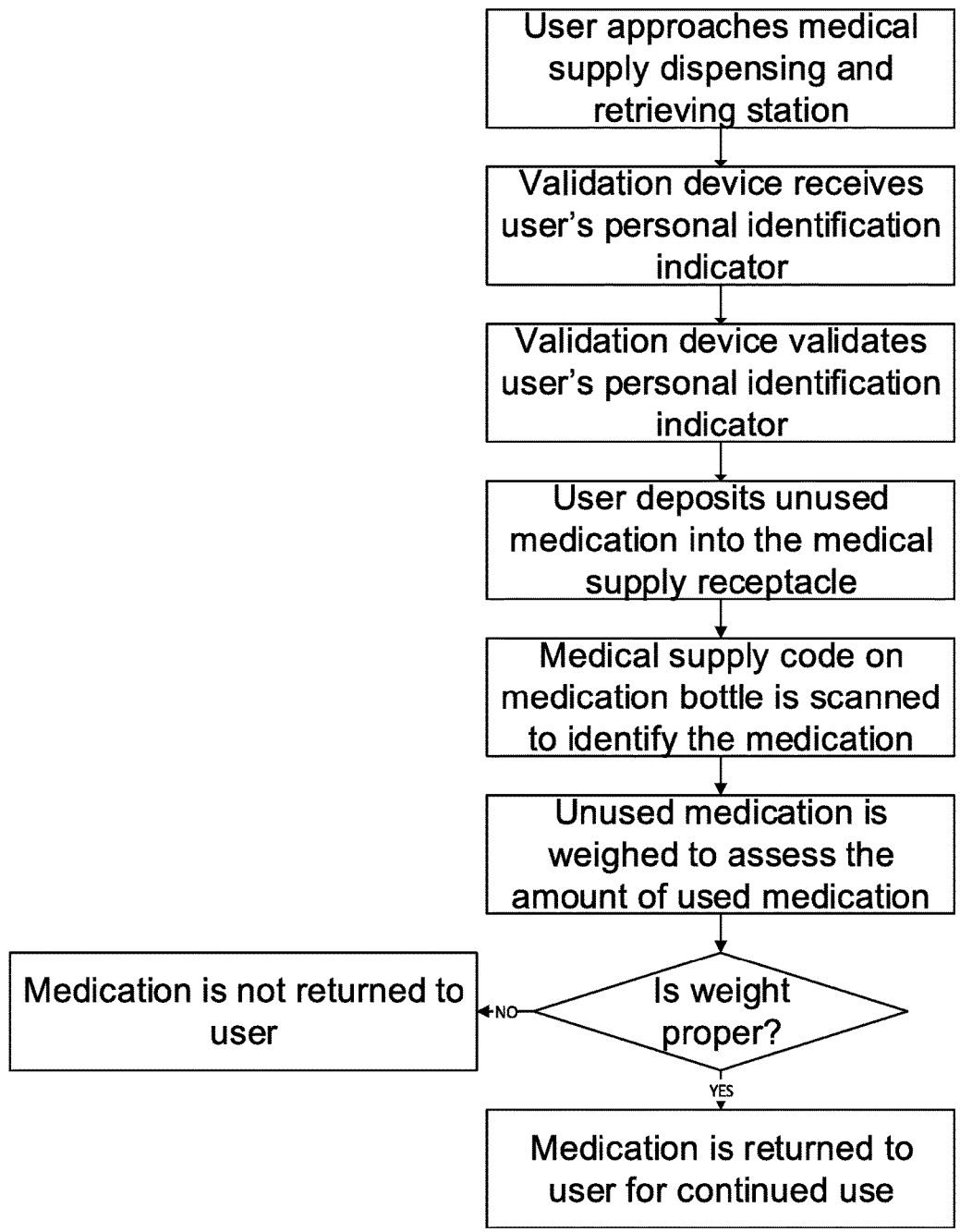
FIG. 8 is a flow chart illustrating a method of using an embodiment of the disclosed medical supply dispensing and retrieving station to confirm proper consumption of a prescription medication.

FIG. 8 is a flow chart illustrating a method that a user may follow to confirm proper consumption of a prescription medication using an embodiment of the disclosed medical supply dispensing and retrieving station. The steps in the method of FIG. 8 may be especially useful in situations when a healthcare provider suspects the user may consume the medical supply too rapidly, as may occur, for example, with medications that may be addictive. In this method, the user approaches the medical supply dispensing and retrieving station and enters a personal identification indicator into the validation device on the medical supply dispensing and retrieving station. The validation device confirms the user's identity and links the information to the user's prescription information stored in the controller as well as the amount of medical supply that should be remaining at the time. The user deposits the unused medical supply into a medical supply receptacle. A scanner scans the medical supply code on the medical supply to identify the medical supply. The medical supply receptacle includes a scale which weighs the unused medical supply. The controller compares the weight measurement to the weight the medical supply would be expected to have if it has been consumed according to instructions provided with the prescription. If the weight is within a defined range of the expected weight, the medical supply dispenser returns the medical supply to the user for continued use. If the weight is outside a defined range of the expected weight, the medical supply dispenser may not return the unused portion of the medical supply to the user.

Figure 9:
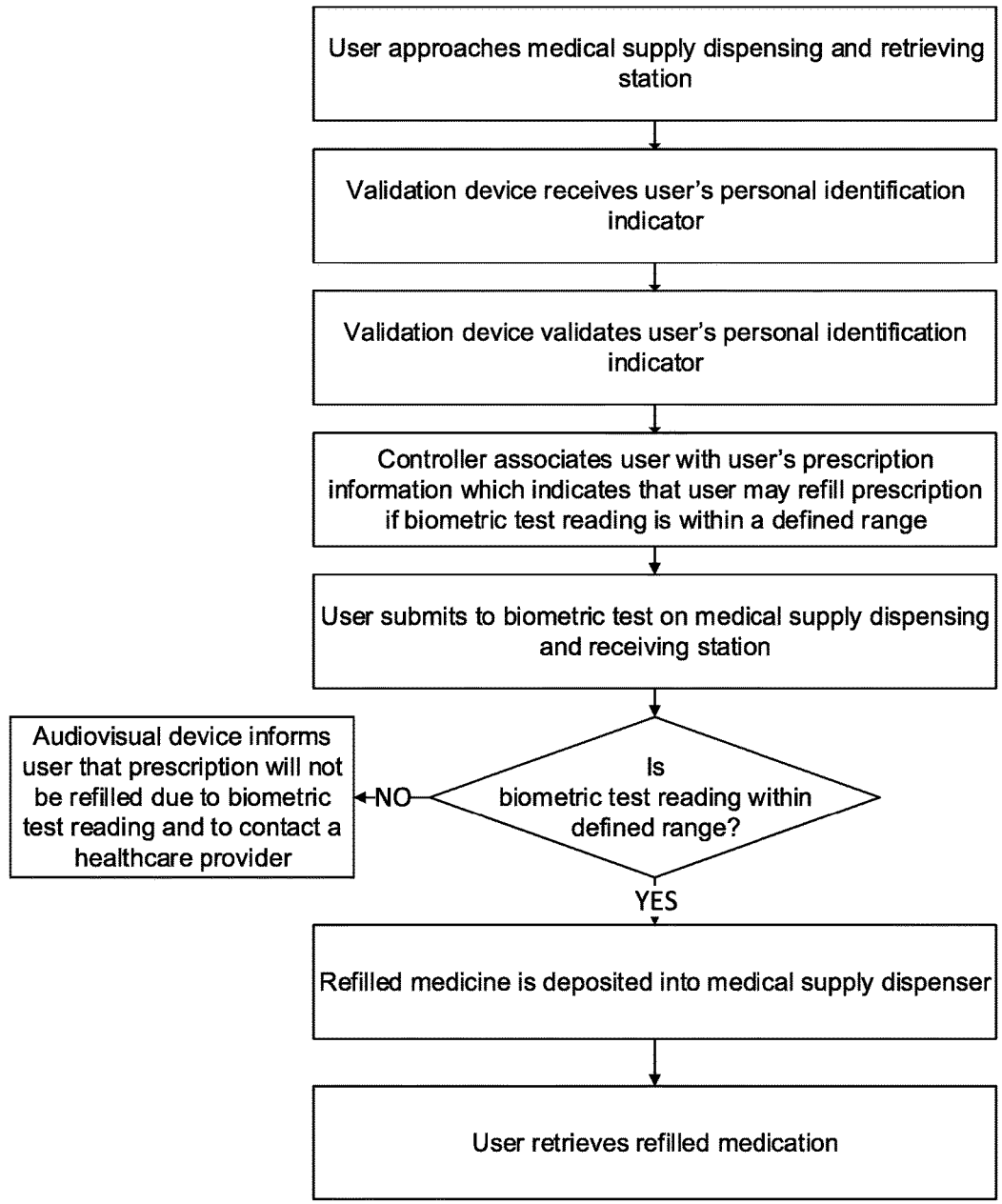
FIG. 9 is a flow chart illustrating a method of using an embodiment of the disclosed medical supply dispensing and retrieving station to refill a prescription medication.

FIG. 9 is a flow chart illustrating a method that a user may follow to refill a prescription for a medical supply using an embodiment of the disclosed medical supply dispensing and retrieving station. In the method of FIG. 9, the user approaches the medical supply dispensing and retrieving station and enters a personal identification indicator into the validation. The validation device confirms the user's identity and links the information to the user's prescription information stored in the controller. The information confirms that the user is authorized to refill the prescription if a specific biometric test reading is within a defined range. The embodiment of the medical supply dispensing and retrieving station includes a medical device which performs the required biometric test or measurement. The user conducts the required biometric measurement using the medical device. If the measurement is within a defined range, the medical supply dispenser provides the refilled medication and the user retrieves the medication for continued use. If the measurement is outside the define range, the prescription may not be refilled. Instead the user is informed through an audiovisual device that the prescription will not be refilled because the biometric test reading is outside of a defined range and that the user should contact a healthcare provider. This method may be used when a prescribed medication is associated with a potentially dangerous side-effect. The user may use the medical supply dispensing and retrieving station to determine if he or she is experiencing the side-effect. The method also prevents the user from continuing to consume the mediation in the presence of the side-effect. Alternatively, the method may be used to determine whether a medication is effective for that user. If the biometric test measurement indicates that the medication is not effective, the method prevents the user from continuing an ineffective treatment and instructs the user to seek further medical intervention. This may lead the user to receive a more effective treatment.

While specific embodiments have been illustrated and described above, it is to be understood that the disclosure provided is not limited to the precise configuration, steps, and components disclosed. Various modifications, changes, and variations apparent to those of skill in the art may be made in the arrangement, operation, and details of the methods and systems disclosed, with the aid of the present disclosure.

Without further elaboration, it is believed that one skilled in the art can use the preceding description to utilize the present disclosure to its fullest extent. The examples and embodiments disclosed herein are to be construed as merely illustrative and exemplary and not a limitation of the scope of the present disclosure in any way. It will be apparent to those having skill in the art that changes may be made to the details of the above-described embodiments without departing from the underlying principles of the disclosure herein.

The invention claimed is:

1. A method of tracking, dispensing, and retrieving medical supplies comprising the steps of:
   providing a user with a personal identification indicator;
   providing a medical supply dispensing and retrieving station, wherein the medical supply dispensing station comprises:
      a user validation device for validating the personal identification indicator;
      a medical supply dispenser, wherein the medical supply dispenser comprises a first plurality of compartments, wherein the first plurality of compartments stores at least one medical supply, wherein the at least one medical supply is tagged with a medical supply code, and wherein the medical supply code is unique each of the at least one medical supply;
      a medical supply receptacle, comprising a second plurality of compartments for storing the at the least one medical supply upon its return;
      a controller;
      at least one biometric measuring device;
      a scale, wherein the scale is positioned to measure a weight of the at least one medical supply;
      a code scanner, wherein the code scanner is positioned to scan the medical supply code as the at least one medical supply enters or leaves the medical supply dispensing and retrieving station; and
      at least one communication port for sending and receiving user and prescription information;
   receiving the at least one medical supply into the medical supply receptacle, wherein the at least one medical supply was previously dispensed by the medical supply dispenser;
   scanning the medical supply code with the code scanner;
   collecting a biometric measurement of the user with the at least one biometric measuring device;
   providing a prescription for a different dosing schedule of at least one of the at least one medical supply in the event that the biometric measurement of the user is outside of a defined range; and
   dispensing the at least one medical supply from the medical supply receptacle and an instruction for the different dosing schedule.

2. The method of claim 1, wherein the user is an individual authorized to receive at the least one medical supply for another individual.

3. The method of claim 1, wherein the personal identification indicator is selected from one or more of the following: a Bluetooth beacon, a personal identification code, a token, a magnetic stripe card, a radio frequency emanating from a mobile device, and a biometric input.

4. The method of claim 1, further comprising the step of sterilizing the at least one medical supply received by the receptacle.

5. The method of claim 1, further comprising the step of destroying the at least one medical supply received by the receptacle.

6. The method of claim 1, further comprising the steps of returning the at least one medical supply to the user for continued use.

7. The method of claim 1, wherein the at least one medical supply comprises at least two medical supplies, and wherein the at least two medical supplies comprises one or more of the following: a prescription medication, an over-the-counter medication, a medical treatment device, a pharmaceutical delivery device, a medical diagnostic device, a medical alert tag, a urinary catheter, and a wound care supply.

8. The method of claim 1, wherein the biometric measurement device comprises one or more of the following: a heart rate monitor, a blood pressure monitor, a weight sensor, a bioimpedance sensor, a glucometer, a blood analyzer, an electrocardiogram unit, a respirometer, a respiratory rate monitor, a body temperature sensor, an otoscope, a stethoscope, a pulse oximeter, an ophthalmoscope, an ultrasound device, a test strip, a test strip reader, and a tissue collector.

9. The method of claim 1, further comprising the steps of supplying at least two medical supplies; and
of reporting to the user that at least one of the at least two medical supplies is no longer medically appropriate and will not be returned in view of the biometric measurement.

10. The method of claim 1, further comprising the step of sending an electronic report through the communication port to a healthcare provider, wherein the electronic report comprises the biometric measurement.

11. The method of claim 1, further comprising the step of dispensing at least one alternative medical supply based on the biometric measurement.

12. The method of claim 1, wherein each of the at least one medical supply is connected to a temperature verifier which indicates whether the at least one medical supply has experienced a temperature outside a defined range.

13. The method of claim 12, further comprising the step of creating a reading of the temperature verifier, associating the reading with the medical supply code, and storing the reading and medical supply code in a file in the controller.

14. The method of claim 13, further comprising the step of flagging each of the at least one medical supply for either destruction or reuse based on the reading of the temperature verifier.

\* \* \* \* \*